US006399095B1

(12) United States Patent
Fujita

(10) Patent No.: US 6,399,095 B1
(45) Date of Patent: *Jun. 4, 2002

(54) TABLETED PRODUCT PREPARED BY VACUUM FREEZE-DRYING OF A PLANT BELONGING TO GENUS ALOE OF FAMILY LILIACEAE AND THE METHOD FOR PRODUCING SAME

(75) Inventor: Keisuke Fujita, Toyoake (JP)

(73) Assignee: Yurika Incorporated, Mie-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/120,194

(22) Filed: Sep. 13, 1993

Related U.S. Application Data

(63) Continuation of application No. 07/713,052, filed on Jun. 10, 1991, now abandoned.

(30) Foreign Application Priority Data

Jun. 13, 1990 (JP) .............................................. 2-152690

(51) Int. Cl.⁷ ................................................. A61K 9/20
(52) U.S. Cl. ........................ 424/464; 424/489; 424/744
(58) Field of Search ................................ 424/464, 489, 424/195.1, 744, 484, 485

(56) References Cited

U.S. PATENT DOCUMENTS

| 3,892,853 A | * | 7/1975 | Cobble | ........................ 424/195 |
| 4,178,372 A | * | 12/1979 | Coats | ......................... 424/195 |
| 4,493,822 A | * | 1/1985 | Torey | .......................... 424/15 |
| 4,966,892 A | * | 10/1990 | McAnalley | .................. 514/54 |
| 4,976,960 A | * | 12/1990 | Grossman et al. | ........ 424/195.1 |
| 5,137,730 A | * | 8/1992 | Dennis et al. | ............... 424/465 |

FOREIGN PATENT DOCUMENTS

| GB | 1199887 | 7/1970 |
| JP | 40-12390 | 9/1963 |
| JP | 56-110626 | 9/1981 |
| JP | 59-78121 | 5/1984 |
| JP | 60-109526 | 6/1985 |
| JP | 61-183227 | 8/1986 |
| JP | 62-5129 | 2/1987 |
| JP | 1-300845 | 12/1989 |
| KR | 735-0606 | 3/1986 |
| WO | WO 89/06539 | 7/1989 |
| ZA | 693391 | 5/1969 |

OTHER PUBLICATIONS

Comments on Doc. No. 1 above, (AA) 59–78121, Japan, 1995.
Comments on Doc. No. 2 above, (AB) 61–183227, Japan, 1995.
Translation of Doc. No. 2 above, (AB), Intestine–Controlling Food, Kokai Publication No. 61–183227 (A), Shigeru Yuchi, K.K. Osaka Yakuhin Kenkyusho, Jul., 1985.
Comments on Doc. No. 3 above, (AC) 1–300845, Japan.
Comments on Doc. No. 5 above, (AE) 735–0606, Korea 1998.

* cited by examiner

Primary Examiner—Neil S. Levy
(74) Attorney, Agent, or Firm—Morrison & Foerster LLP

(57) ABSTRACT

A vacuum freeze-dried mass of a plant belonging to the genus Aloe of the family Liliaceae, a vacuum freeze-dried granule of the plant, a tablet formed by a vacuum freeze-dried mass of the plant, a medicine formed by the tablet, and the method for producing the vacuum freeze-dried mass, the vacuum freeze-dried granule, the tablet and the medicine. The vacuum freeze-dried product maintains the inherent properties of living aloe useful for medicine or health food.

8 Claims, No Drawings

TABLETED PRODUCT PREPARED BY VACUUM FREEZE-DRYING OF A PLANT BELONGING TO GENUS ALOE OF FAMILY LILIACEAE AND THE METHOD FOR PRODUCING SAME

This application is a continuation of U.S. application Ser. No. 07/713,052 filed Jun. 10, 1991, now abandoned.

FIELD OF THE INVENTION

This invention relates to a tablet prepared from a dried product obtained by pulverization under cooling and subsequent vacuum freeze-drying of a fresh entire aloe leaf, a method for preparing the tablet, and use thereof.

The tablet according to the present invention is useful as a medicine or so-called health food, such as laxative, stomachics, anti-gastrointestinal ulcer drug, anti-inflammatory drug, anti-fungal drug, anti-hyperglycemia drug, anti-burn edema drug for oral administration, or immunomodulator.

BACKGROUND

Aloe has been extensively used as folk medicine. Reference to aloe powders is also made in the Japanese Pharmacopeia.

The present inventors and laboratories both in Japan and abroad have succeeded in separating low-, medium- and high molecular weight ingredients contained in aloe.

For example, it is known that Aloe arborescens var. natalensis (referred to as "Kidachi aloe" hereinafter) contains polysaccharides such as aloetin, aloenin, aloeursin or D-mannose, aloemannan or aloe albonacite: aloe vera contains polysaccharides; and that Cape aloe contains anthraquinonic ingredients, such as aloin or aloe-emodin.

with this in mind, attempts have intensively been made to process the aloe into medicines. Presently, as the officially allowed health food, food products prepared from Kidachi aloe have been commercialized in Japan extensively.

Most of these products, however, are prepared by drying aloe leaves under sun shine or by hot air and, at the time of tableting, 7–10% of an additive, such as Avicel (Trade name of micro crystalline cellurose) or corn starch, is added as a binder to facilitate tableting.

DISCUSSION OF THE RELATED ART

It is noted that most ingredients that are isolated and purified from the aloe and found to be efficaceous to animals by animal experiments, are polysaccharides, glycoproteins or enzymes, all of which may exhibit activity in a stable state only when treated for purification at lower temperatures. For this reason, it is generally thought to be desirable to apply as small a quantity of heat as possible for the preparation of the health food or medicine from aloe.

However, since the products now presented to the market are prepared by drying aloe leaves under sun shine or by circulation of hot air, the above mentioned components, namely the polysaccharides, glycoproteins or enzymes, have been thermally degraded or oxidized in the course of drying.

Furthermore, the additives for facilitating tableting, such as Avicel or corn starch, are added in an amount of 7–10% in the conventional aloe tablet products. Since a small amount of water is added under heating to knead the additives with the dried aloe mass, the resulting product undergoes further thermal degradation by such heating.

SUMMARY OF THE DISCLOSURE

It is therefore an object of the present invention to provide a dried mass or powder, granule, tablet or a medicine of a plant belonging to the genus Aloe of the family Liliaceae, which is free from the above described inconveniences in the conventional preparation of Aloe product.

It is another object of the present invention to provide a method for producing the dried mass or powder, granule, tablet or medicine.

According to the present invention, the above object is accomplished by the following dried mass, granule, tablet, and medicine and a method for producing the dried mass, granule, tablet and medicine.

i) A vacuum freeze-dried mass of a plant belonging to the genus Aloe of the family Liliaceae.

ii) A method for producing a dried mass of a plant belonging to the genus Aloe of the family Liliaceae comprising crushing the plant and freeze-drying the crushed mass in vacuum.

iii) A vacuum freeze-dried granule of a plant belonging to the genus Aloe of the family Liliaceae.

iv) A method for producing a granule of a plant belonging to the genus Aloe of the family Liliaceae comprising molding the dried mass according to item i) under pressure for granulating.

v) A tablet comprising a vacuum freeze-dried mass of a plant belonging to the genus Aloe of the family Liliaceae.

vi) A method for producing a tablet comprising tableting the granule according to item iii).

vii) A tablet according to item v) further comprising nutrient and/or medicinal ingredients.

viii) A method for producing a tablet comprising tableting the granule according to item iii) with nutrient or medically effective ingredients.

ix) A medicine comprising the tablet according to item v) or vii).

The dried mass, granule or tablet according to the present invention exhibits the following properties:

i) It has a pale green color;

ii) It has a grassy smell;

iii) It has a strongly bitter taste;

iv) It is soluble in water, while being partially insoluble in methanol, ethanol or acetone;

v) In protein determination reactions, it is positive both in bicinchoninic acid (BCA) reaction and in Lowry-Folin reaction;

vi) With regard to saccharides determination reactions, it is positive in anthrone sulfuric acid reaction and in phenol sulfuric acid reaction;

vii) With regard to proteolytic enzyme activities, it has activities of carboxypeptidase and trypsin, and it has also protease-inhibitory activity;

viii) It exhibits positive cell agglutination activity with erythrocytes and weakly positive cell agglutination activity with cancer cells; and ix) It exhibits weakly positive blastogenetic activity with lymphocytes.

The dried mass, granule and tablet of the plant belonging to the genus Aloe of the family Liliaceae according to the present invention contains efficaceous ingredients endogenously contained in the genus Aloe of the family Liliaceae, such as polysaccharides, glycoproteins and enzymes, in a state substantially free from degradation otherwise caused by heating, such as thermal degradation or oxidation. A variety of physiologically active substances, found to be contained in the plant by animal experiments, such as aloin or aloe carboxypeptidase, are also present without undergoing thermal degradation. Hence, the dried mass, granule and tablet according to the present invention may be used as medicines, such as laxative, stomachics, anti-gastrointestinal ulcer drug, anti-inflammatory drug, anti-fungal drug, anti-hyperglycemia drug, anti-burn edema drug, or immunomodulator, or in a variety of health foods.

The tablet of the present invention may consist of 100% of the above mentioned dried mass, without needing an additive for tableting as an essential constituent, so that a high quality tablet is provided which contains the efficaceous or medicinal ingredients of the plant belonging to the genus Aloe of the family Liliaceae with a high purity.

The tablet of the present invention is easy to swallow, even though it has a strong bitter taste and a flavor displayed by the plant when chewed.

In the present method for producing the dried mass of the present invention, the liquid obtained by crushing the plant belonging to the genus Aloe of the family Liliaceae is freeze-dried in vacuum, without resorting to the step of drying the liquid by heating it at a temperature higher than the ambient temperature, therefore, the dried mass containing the above mentioned efficaceous ingredients in the plant is prepared without degrading those ingredients.

According to the method for preparing the granule of the present invention, the dried mass is press molded into the granule. The granule contains the efficaceous ingredients without thermally degrading these efficaceous ingredients.

In the method for producing the tablet of the present invention, the dried mass is press molded into the granule, and then tableted. Thus, the tablet containing the above mentioned efficaceous ingredients is produced without degrading the efficaceous ingredients in the plant. Since no additive for facilitating tableting is required, the tablet containing the above efficaceous ingredients in higher percentages are produced. Thus the tablet contains up to 100 percent of effective ingredients.

In this method for preparing the tablet in the present invention, the granule can be tableted with the fortified nutrient or medicinal ingredients, not originally contained in the plant. Thus the nutrients or medicinal ingredients originally contained in the plant can be supplemented to be found in increased concentrations in the produced tablet.

DESCRIPTION OF THE PREFERRED EMBODIMENT

Dried Mass

The vacuum freeze-dried mass of a plant belonging to the genus Aloe of the family Liliaceae, such as Kidachi aloe, Aloe vela or Cape aloe, is obtained by freeze-drying a liquid obtained by crushing the plant. The dried mass obtained in this manner is usually in the flocculated state and is easily pulverized, for example, by charging the mass into a bag. The specific gravity of the dried mass is usually from 0.085 to 0.090.

Method for Preparing the Dried Mass

The liquid obtained by crushing the plant is obtained by crushing the plant with the use of, for example, a homogenizer. Since the heat is generated during homogenization, the outer side of the homogenizer is cooled by ice water.

The entire time for freeze-drying the crushed liquid in vacuum is about 30 hours. The vacuum degree, expressed in terms of the pressure of the remaining gas, is less than 0.4 mbar, not more than 0.2 mbar, and not more than 0.1 mbar during the initial ten hours, during intermediate ten hours, and during the final ten hours, respectively. The temperature of the crushed and freezed liquid during drying is not higher than $-20°$ C., and preferably not higher than $-40°$ C. during the above mentioned initial and intermediate periods, and gradually raised from minus $-40°$ C. to ambient temperature, e.g., plus $+25°$ C., during the period of ten hours from the start until the end of the final drying period. This enables the moisture to be vaporized off to provide a completely dried mass. According to the method of the present invention, the temperature at the end of the final drying period is are ambient temperature, e.g., from plus $+20°$ C. to plus $25°$ C.

Granule

The particle size of the granule for producing the tablet preferably range from 18 to 20 mesh, and the specific gravity of the granule preferably ranges from 0.65 to 0.75.

Method for Producing the Granule

The granule is produced by press molding (or compacting) the dried mass under a pressure of, for example, 150 kgf/cm$^2$. The granules having a specific gravity of 0.74, produced by press molding under the above pressure. Granulation may be carried out by using a commercially available granulator.

Tablet

The tablet may be in the form of, for example, a cylindrical column with a length of 5 mm and a diameter of 5 mm.

Preferably, the tablet weighs 130 to 150 mg, and has a specific gravity of 1.3 to 1.5.

The tablet may contain nutrient or medicinal ingredients not originally contained in or contained only in a limited quantity in the genus Aloe of the family Liliaceae. For example, the tablet may contain garlic powders or vitamin C.

Method for Producing the Tablets

The tablets may be produced by tableting granules which contain endogenous nutrient and/or medicinal ingredients in the plant of the genus Aloe of family Liliaceae, or a mixture of the granules and the powders or granules of the other nutrient or medicinal ingredients. The tableting may be carried out, for example, at a pressure of 600 kgf/cm$^2$, resulting in a specific gravity of about 1.3 when the granules alone.

About 11 kg of fully grown leaves of Kidachi aloe, cultivated for about three to four years, with each leaf weighing about 100 to 120 g, are collected.

These leaves are washed thoroughly with a scrubbing brush and, after the thorns and white hard fibers at the leaf roots are removed by a cutter, and the remaining portions of the leaves are washed with distilled water.

The leaves weigh about 9 kg at this time, so that, with 9 kg, corresponding to a volume of 9 liters, of the aloe leaves as one unit, the leaves are cut into small pieces and charged into a homogenizer to produce a crushed aloe liquid, referred to hereinafter as aloe juice.

Since the capacity of a vacuum freeze-drying tray for KYOWA vacuum freeze-drier RLE 203 is 3 liters, the homogenate weighing 9 kg is divided into three fractions.

The three aliquotes of homogenates are frozen at minus 30° C. to minus 40° C. and charged into a freeze-drier. The 9 liters of the aloe juice were dried in about 30 hours by the KYOWA vacuum freeze-drier RLE 203 to produce 360 g of dried powders.

These powders are charged into a dry granulator, such as a roll compactor, for granulation. The volume of the powders at this stage is reduced to about one tenth.

If the granules are not of the uniform size, the tableted product tends to fluctuate in quality. In order to prevent this, granulation by the roll compactor may be repeated two or three times.

The granules are tableted immediately on a tablet machine. If tableting is to be achieved without additives, each tablet preferably weighs about 130 to 150 mg.

In this manner, about 350 g of the vacuum freeze-dried powders are produced from the batch of 9 kg of the aloe juice, so that about 2,600 tablet products are produced.

A about 3–10% of an additive, such as Avisel or corn starch, is added in the conventional aloe tablet to facilitate tableting. Also, a humidifier such as water or alcohol is added to the powders and kneaded with the additive and the resulting mixture is formed into a tablet through drying with hot air.

On the contrary, according to the present invention, the dry granulator, such as the roll compactor, is used to eliminate the kneading step for granulation as well as to raise the density of the mass to facilitate the subsequent tableting.

According to the above described method of the present invention, the aloe powders are formed into tablets without using an additive as a binder.

The tablets prepared from the vacuum freeze-dried aloe powders are in the form of a cylindrical column with a length of 5 mm and a diameter of 5 mm.

The tablets have a fresh pale green color and a bitter taste similar to that of the fresh aloe leaf. On the other hand, conventional aloe tablets, produced by drying at a higher temperature, are excessively oxidized, have a pale yellow to brownish color, and have a bitter taste somewhat different from the taste of the fresh aloe. This is due to increased oxidized derivatives of aloin, calcium succinate salt, which is yellowish and is mainly composed of barbaloin, i.e., anthrone C glycoside.

Comparative Test Between Inventive and Conventional Products

The inventive product and the conventional product (control) were compared with respect to test items (a) to (h), as shown in Table 1.

As the inventive product, the tablets produced in the preceding example were employed. As the control product, commercially available conventional aloe tablets were used. These tablets were prepared by drying under hot air circulation and subsequently tableting a dried mass obtained by admixing an additive for facilitating tableting, such as Avicel or corn starch, and a humidifier, such as water or alcohol, to dried aloe leaves.

TABLE 1

| Test items | Inventive | Control |
| --- | --- | --- |
| (a) Color | Pale green color | Yellowish green color |
| (b) Smell | Strong grassy smell | Grassy smell |
| (c) Taste | Strong bitter taste similar to that of green raw leaf | Bitter taste |
| (d) Solubility | Soluble in water, partially insoluble in organic solvent | Same as inventive product |
| (e) Protein determination reaction | | |
| 1) BCA reaction | 15.7 mg/ml* | 4.1 mg/ml* |
| 2) Lowry-Folin reaction | 20.2 mg/ml* | 6.5 mg/ml* |
| (f) Saccharide determination reaction | | |
| 1) Anthrone-Sulfulic Acid reaction | 13.6 mg/ml* | 8.0 mg/ml* |
| 2) Phenol-Sulfulic Acid reaction | 48.0 mg/ml* | 30.5 mg/ml* |
| (g) Proteolytic enzyme | | |
| 1) Carboxypeptidase | 5.4 U/ml* | 0.69 U/ml* |
| 2) Trypsin | 18.1 µg/ml* | 0.5 µg/ml* |
| 3) Protease inhibitory (pepsin inhibitory) activity | 42% | 5% |
| (h) Erythrocyte agglutination activity, human O-type | 16 titer | 2 titer |

*1.0 g of tablet was dissolved into 10.0 ml of distilled water and was measured by each reaction, ml represents 1.0 ml of this solution.

The methods for the tests on the items (e) to (h), the results and their significances are summarized as follows:

(e) Protein Determination Reaction

The inventive tablet product and the control tablet product obtained under drying in hot air were crushed into powders. 1.0 g each of the tablets were dissolved in 10 ml of distilled water, stirred and centrifuged at 12,000 rpm for 30 minutes at 4° C. The total protein in the produced supernatant was determined by the bicinchoninic acid method (BCA method), using a protein assay reagent kit. manufactured by PIERCE, U.S.A. as described by Smith, P. K. et al (Measurement of Protein Using Bicinchoninic Acid. Anal. Biochem. (1985) 150. 76–85), and also by the Lowry-Folin method, as described by Lowry et al. (Protein Measurement with the Folin Phenol Reagent, J. Biol. Chem. (1951) 193. 265–275).

The results of the analyses have revealed that the inventive product contained 15.7 mg of the protein per each 1 ml of a liquid extract, as measured with the BCA method, whereas the protein content of the control product was 4.1 mg.

The protein content of the inventive product, as measured by the Lowry-Folin's method, was 20.2 mg, whereas that of the control product was 6.5 mg.

The results show that the inventive product contains natural proteins more abundantly and that the amount of the aloe material per unit weight is higher in the inventive product because of the absence of the additive(s).

(f) Saccharide Determination Reaction

The inventive tablet product and the control tablet product obtained under drying in hot air were crushed into powders. 1.0 g of each of the powdered tablets was dissolved in 10 ml of distilled water, stirred and centrifuged at 12,000 rpm for 30 minutes at 4° C. Saccharide determination tests were conducted on the produced supernatents by the anthrone-sulfuric acid reaction with respect to the monosaccharide, as described by R. Drywood (Ind. Eng. Chem., Anal. Ed., 18.

499 (1946)), and also by the phenol-sulfuric acid reaction for oligosaccharides, polysaccharides or glycoprotein, as described by M. Dudols et al. (Anal. Chem., 28. 350 (1956)).

A large amount of hexose, such as glucose, is contained in both the inventive and control products, as indicated by strong anthrone-sulfuric acid reaction with green to blue green color.

The hexose concentration, calculated as glucose, was 13.6 mg/ml and 8.0 mg/ml for the inventive and control products, respectively.

Both the inventive and control products present a yellow-brown color in the phenol-sulfuric acid reaction, and the concentration, measured as glucose, was 48.0 mg/ml and 30.5 mg/ml for the inventive and control products, respectively.

It is shown that the succharides originating from the glycoprotein and polysaccharides remain in the inventive product.

(g) Proteolytic Enzyme Activity

Three proteolytic enzymes have been isolated from Kidachi aloe by the present inventors. Since these enzymes are the heat-labile proteins or glycoproteins, it is crucial from the viewpoint of the product quality whether these enzymes remain in fact in the inventive product.

The inventive tablet product and the tablet product of the control obtained by drying under hot air circulation were crushed into powders. Then, 1 g each of the powders was dissolved in 10 ml of distilled water, stirred and centrifuged at 12,000 rpm for 30 minutes at 4° C. The supernatents were subjected to the following activities tests.

i) Test on Carboxypeptidase Activity

Bradykinin or Z-Phe-Tyr, Z-Gly-Pro-Leu-Gly was incubated with 50 µl of the supernatants of the inventive and control products at 37° C. for one hour at pH 5.0, and the products, amino acids, were subjected to a ninhydrin reaction to measure the enzyme activity.

The reaction with Z-Gly-Pro-Leu-Gly as substrate revealed that the inventive product and the control product exhibit the carboxypeptidase activity 5.4 units and 0.69 unit per 1 ml of the supernatant, respectively.

The inventive product thus exhibits enzyme activity of carboxypeptidase even after tableting. Carboxypeptidase enzyme exhibits anti-inflammatory effects and anti-edematous effects on burn and is capable of effectively decomposing bradykinin, the chemical mediator of inflammation.

2) Trypsin Activity

A proteolytic enzyme similar to trypsin was separated by the present inventors from Kidachi aloe.

N-Benzoil alginine p-nitroanilide or acetyl alginine p-nitroanilide was incubated with 200 µl of the inventive and control products at 37° C. at pH 8.0 for three hours.

The results of the measurement of isolated p-nitroaniline revealed that the inventive and control products contained p-nitroaniline in amounts of 18.1 µg/ml and 0.5 µg/ml, respectively, thus indicating that trypsin remains in the inventive product without loss of its activity.

Trypsin exhibits similar reactivity as enterokinase, thrombin, plasmin or kallikrein. It has been known that trypsin separated from actinomyces exhibits anti-inflammatory effects when administered orally.

3) Protease Inhibitor

200 µl of the supernatants of the inventive and control products, or distilled water, were added to 1 ml of casein as a substrate, respectively, and the reaction was continued under pH 2.0 at 37° C. for three minutes. Then 0.1 ml of the pepsin solution was added to the reaction system arid the reaction was further carried out for 30 minutes.

For termination of the reaction, 2 ml of 1.7M perchloric acid solution was added, and the resulting mixture was centrifuged. Absorbance of the supernatants was measured at a wavelength of 280 nm.

With the absorbance of the reaction system, added to by the distilled water, equal to 100%, the absorbance of the inventive product was 142%, while that of the control product was 105%. The inventive and the control products inhibited the reaction of pepsin with casein as substrate by 42 percents and 5 percents, respectively. Thus, the pepsin inhibitor activity was found to persist in the inventive product.

The presence of the pepsin inhibitor in the inventive product indicates that pepsin in gastric ulcer may be inhibited by oral administration of the inventive product.

(h) Erythrocyte Agglutination

The inventive tablet and the control tablet obtained by drying under hot air circulation, were crushed into powders. 1.0 g each of the powders was dissolved in 10 ml of distilled water. After stirring, each of the resulting solutions was centrifuged at 4° C. for 30 minutes at 12,000 rpm.

The erythrocyte agglutination activity of each of the produced supernatants was examined in accordance with the microtiter method.

A buffer solution obtained by mixing phosphoric acid with physiological saline to pH 7.4 was added to 100 µl each of the supernatants for two-stage dilution until 128-fold dilution was reached. To each diluted solution, 100 µl of the 1% human O-type erythrocytes were added, and reaction was carried out at 37° C. for one hour to observe the progress of agglutination.

It was found that the agglutination titer of the inventive product was 16 titer, while that of the control product was 2 titer. The agglutination titer of Concanavalin A, used as control, was 32 titer, at a concentration of 1 mg/ml.

Therefore, the substance termed lectin which produces erythrocyte agglutination as Concanavalin A is contained at a higher concentration in the inventive tablet.

Lectin has been demonstrated to specifically agglutinate tumor cells and to exhibit cytotoxity, or as to modulate immune-related cells, such as promotion of blastogenesis or differentiation of lymphocytes.

These results prove that the inventive product contains a larger quantity of lectin than in the control product.

What is claimed is:

1. A vacuum freeze-dried mass, consisting of freeze dried ingredients, wherein said freeze mass is made by homogenizing an entire leaf free from material derived from stems of a plant belonging to the genus Aloe of the family Liliaceae to produce a homogenized Aloe liquid and then freeze-drying said homogenized Aloe liquid in a vacuum to produce said vacuum freeze-dried mass.

2. A vacuum freeze-dried mass according to claim 1, which is in the form of granule.

3. A tablet consisting of a vacuum freeze-dried mass made by homogenizing under cooling an entire leaf free from material derived from stems of a plant belonging to the genus Aloe of the family Liliaceae to produce a homogenized Aloe liquid and then freeze-drying said homogenized Aloe liquid in a vacuum to produce said vacuum freeze-dried mass, said mass consisting of freeze dried ingredients of said entire leaf and being free from enzyme decomposition products.

4. A tablet consisting of a vacuum freeze-dried mass and a nutrient and/or medicinal ingredient, wherein said freeze dried mass is made by homogenizing under cooling an entire leaf free from material derived from stems of a plant belonging to the genus Aloe of the family liliaceae to produce a homogenized Aloe liquid and then freeze-drying said homogenized Aloe liquid in a vacuum to produce said vacuum freeze-dried mass, said mass consisting of freeze dried ingredients of said entire leaf and being free from enzyme decomposition products.

5. A medicine consisting of a vacuum freeze-dried mass made by homogenizing under cooling an entire leaf free from material derived from stems of a plant belonging to the genus Aloe and the family Liliaceae to produce a homogenized Aloe liquid and then freeze-drying said homogenized Aloe liquid in a vacuum to produce said vacuum freeze dried mass, said mass consisting of freeze dried ingredients of said entire leaf and being free from enzyme decomposition products.

6. A medicine as claimed in claim 5, wherein said medicine is in the form of a tablet.

7. A tablet as claimed in claim 3, wherein said tablet has a specific gravity of at least 0.65.

8. A medicine as claimed in claim 5, wherein said tablet has a specific gravity of at least 0.65.

* * * * *